United States Patent [19]
Guo

[11] Patent Number: 5,389,674
[45] Date of Patent: Feb. 14, 1995

[54] FUNGICIDAL COMPOSITIONS AND METHODS FOR PRODUCTION THEREOF

[75] Inventor: Yili Guo, Maple Glen, Pa.

[73] Assignee: Rohm and Haas Company, Philadelphia, Pa.

[21] Appl. No.: 90,599

[22] Filed: Jul. 12, 1993

Related U.S. Application Data

[63] Continuation-in-part of Ser. No. 877,010, May 1, 1992, abandoned.

[51] Int. Cl.$^6$ ............ A01N 47/14; A01N 55/02; A01N 25/12
[52] U.S. Cl. ............ 514/476; 514/483; 514/492; 514/494
[58] Field of Search ............ 514/483, 476, 492, 494

[56] References Cited

U.S. PATENT DOCUMENTS

| | | | |
|---|---|---|---|
| 2,848,297 | 8/1958 | Hill | 21/2 |
| 3,497,598 | 2/1970 | Luginbuhl | 424/287 |
| 3,737,551 | 6/1973 | Karsten et al. | 424/286 |
| 3,992,548 | 11/1976 | Pommer et al. | 424/274 |
| 4,476,113 | 10/1984 | Young et al. | 424/116 |
| 4,584,309 | 4/1986 | Ishiguri et al. | 514/383 |
| 4,936,901 | 6/1990 | Surgant, Sr. et al. | 71/92 |
| 5,001,150 | 3/1991 | Yap | 514/476 |

Primary Examiner—Allen J. Robinson
Assistant Examiner—S. Mark Clardy
Attorney, Agent, or Firm—Joseph F. Leightner

[57] ABSTRACT

Novel and improved fungicidal dithiocarbamate particulate compositions comprising one or more components selected from dithiocarbamates and bisdithiocarbamoyl disulfides and an effective amount of moisture content to significantly enhance the flowability of the particulate composition, reduce the dustiness of the composition, increase the bulk density of the composition and/or reduce the ethylenethiourea content of the composition. Methods for producing such particulate compositions are presented wherein controlled slurry production and spray-drying are effective in producing such compositions.

33 Claims, 1 Drawing Sheet

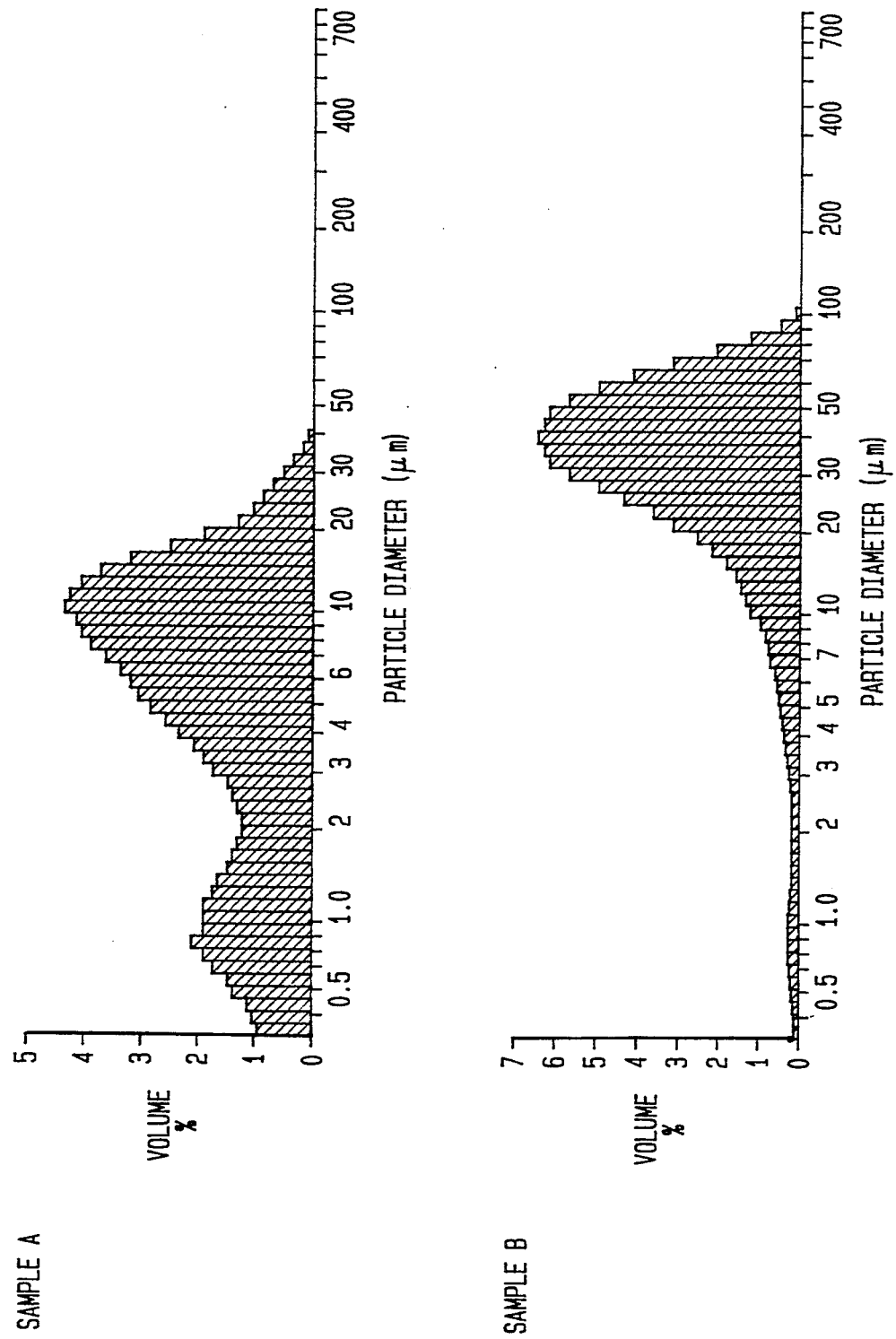

FUNGICIDAL COMPOSITIONS AND METHODS FOR PRODUCTION THEREOF

This application is a continuation-in-part of application Ser. No. 07/877,010, filed on May 1, 1992, now abandoned.

BACKGROUND

Fungicidal dithiocarbamate and bisdithiocarbamoyl disulfide compounds have utility when contained in particulate compositions as powders or granules. Such powders or granules often are dispersed, dissolved or otherwise mixed into liquids to form slurries or other mixtures for use in agricultural sprays. Such mixtures are frequently made at the site of application after prior storage of the particulate compositions.

The storage, handling, dispersing and applying of such dithiocarbamate and bisdithiocarbamoyl disulfide compositions can have attending complications and problems. Such problems can require the use of stabilizing agents to prevent degradation during storage; costly binders or production methods to reduce attrition and undersizing of particles leading to dustiness and product loss; dispersing, wetting and surfacing agents; and mechanical methods to assist in formulating and handling spray mixtures. Also desired is the minimization of undesirable by-products, for example ethylenethiourea (ETU), created during these activities. There continues to be a need for fungicidal dithiocarbamate and bisdithiocarbamoyl disulfide compositions with improved characteristics as well as for methods of producing such compositions.

SUMMARY OF THE INVENTION

Novel and improved fungicidal dithiocarbamate and bisdithiocarbamoyldisulfide particulate compositions are embodied in this specification. Such compositions comprise a fungicidally effective amount of one or more components selected from dithiocarbamates and bisdithiocarbamoyl disulfides and an effective amount of moisture content to significantly enhance the flowability of the particulate composition, reduce the dustiness of the composition, increase the bulk density of the composition and/or reduce the ethylenethiourea content of the composition. Methods for producing such dithiocarbamate and bisdithiocarbamoyldisulfide particulate compositions are presented wherein controlled slurry production and spray-drying are effective in producing such compositions with enhanced properties. Such methods are novel and provide economical benefits in addition to the enhanced characteristics of the produced compositions.

FIGURES

FIG. 1 depicts two particle size distribution charts for a Sample A (low moisture compositions) and Sample B (controlled moisture compositions).

DESCRIPTIONS OF THE PREFERRED EMBODIMENTS

COMPOSITIONS

One embodiment of the present invention is a particulate composition comprising a fungicidally effective amount of one or more components selected from dithiocarbamates and bisdithiocarbamoyl disulfides and an effective amount of moisture content to significantly enhance flowability of said particulate composition. More preferably, the amount of moisture content is optionally effective to reduce the dustiness of the composition, increase the bulk density of the composition and/or reduce the ethylenethiourea content of the composition when ethylenethiourea is a producible product of compounds present in the composition.

Preferably, the one or more dithiocarbamate(s) of the embodied composition is selected from ethylenebisdithiocarbamate metal salts, dimethyldithiocarbamate metal salts, and propylenebisdithiocarbamate metal salts. Preferred ethylenebisdithiocarbamate metal salts are mancozeb {a coordination product of zinc and manganese ethylene bisdithiocarbamate}, maneb {manganese ethylenebisdithiocarbamate} and zineb {zinc ethylenebisdithiocarbamate}. A preferred dimethyldithiocarbamate metal salt is ziram {zinc dimethyldithiocarbamate}. A preferred propylene-bisdithiocarbamate metal salt is propineb {[[(1-methyl-1,2-ethanediyl) bis[carbamatothioato]](2-)]zinc homopolymer}. Another preferred dithiocarbamate is metiram {tris[amine[ethylene bis(dithiocarbamato)]zinc(II)][tetrahydro-1,2,4,7-dithiadia-zocine-3,8-dithione]polymer}. A preferred bisdithiocarbamoyl disulfide is thiram {bis(dimethylthiocarbamoyl)disulfide}. These preferred metal salt(s) and bisdithiocarbamoyl disulfide may be present singularly or in combinations.

Preferably, the total weight of the components selected from dithiocarbamates and bisdithiocarbamoyl disulfides is from about 20 to about 95 weight percent of the embodied particulate compositions; more preferably, at least about 50% by weight; and even more preferably, at least about 80% by weight.

The moisture content of embodied compositions has unexpectedly provided valued benefits. The moisture content can be a wide variety of material in liquid or vapor form and in a chemically bonded, hydrated or unhydrated state. In one preferred embodiment, the moisture is comprised of one or more component(s) selected from water, alcohol, ammonia, carbon disulfide and glycol. More preferably, the moisture content is predominantly water. The moisture content is preferably from about 2.5 to about 20% of the embodied particulate compositions by weight, more preferably about 2.5 to about 10% of the embodied particulate compositions by weight. In one preferred embodiment the moisture content is predominantly water of hydration.

Embodied compositions can have significantly enhanced flowability relative to compositions not having moisture content from about 2.5 to about 20% by weight of the embodied particulate compositions. Preferably the flowability of embodied compositions is such that the angle of repose for such compositions is less than about sixty degrees from the horizontal.

Embodied compositions after production can have an initial ethylenethiourea content of less than about 0.1 weight percent of the total composition weight. One preferred embodiment is a composition wherein the dithiocarbamate comprises mancozeb and the initial ethylenethiourea content is from about 0.01 to about 0.05 weight percent of the total composition weight. More preferably, the ethylenethiourea content of the particulate composition maintained at a temperature of about 54° C. for two weeks after production of the composition is less than about 0.3 weight percent, more preferably from about 0.10 to about 0.25 weight percent, even more preferably less than about 0.20 weight percent of the total composition weight. Another embodied composition maintained at a temperature of about 54° C. for four weeks after production of the composition has an ethylenethiourea content of less than about 0.3 weight percent, more preferably less than about 0.15 weight percent of the total composition weight.

Embodied compositions preferably have a bulk density of at least about 0.5 gram per cubic centimeter, more preferably at least about 0.75 gram per cubic centimeter, even more preferably from about 0.75 to about 1.0 gram per cubic centimeter.

Embodied compositions preferably have a dry particle median size range of from about 20 to about 400 micrometers ($\mu$m). Preferably, the particle size and distribution is such that the embodied composition has a significantly reduced dustiness, that is, reduced volume of particles with particle diameters less than about 5 micrometers, more preferably less than about 10 micrometers, such that at least about 50 per cent by volume of the particles have a diameter greater than 5 micrometers, more preferably 10 micrometers. In one embodiment the volume percent amount of dry particles less than about 15 micrometers is at most about 50 percent of the volume percent amount of dry particles present when the composition is dried to 1 percent moisture content. More preferably, the volume percent amount of dry particles less than 15 micrometers is at most about 25 percent of the volume percent amount of dry particles present when said composition is dried to 1 percent moisture content. Also in some preferred embodiments the volume percent amount of dry particles greater than about 20 micrometers is at least about 50 percent of the volume percent amount of dry particles present when said composition is dried to 1 percent moisture content.

A preferred embodiment is a composition comprising (a) particles comprising one or more components selected from ethylenebisdithiocarbamate metal salts, dimethyldithiocarbamate metal salts, propylenedithiocarbamate metal salts, metiram and thiram, and (b) water; wherein the total weight of said components is from about 20 to about 90 weight per cent of said composition and wherein said composition has a bulk density of at least about 0.5 gram per cubic centimeter and the character of an angle of repose of at most about sixty degrees and wherein at least about fifty per cent by volume of said particles as dry particle have a diameter greater than five micrometers.

METHODS

Other embodiments of the present inventions include methods for the production of the embodied compositions. One embodied method is a method for producing a particulate composition comprising from about 20 to about 95 weight percent of the embodied particulate compositions of components selected from dithiocarbamates and bisdithiocarbamoyl disulfides, said method comprising (1) creating a slurry comprising particles of said components selected from dithiocarbamates and bisdithiocarbamoyl disulfides, said particles having a median particle size of from about 2 to about 7 micrometers; and (2) spray-drying said slurry to produce said particulate composition with a moisture content of from about 2 to about 10 weight percent of the embodied particulate compositions;

said creating and spray-drying being effective to significantly enhance the flowability of said particulate composition.

One preferred embodiment is the method wherein said dithiocarbamate is mancozeb. In such method in the slurry said particles preferably can have a median particle size of from about 3 to about 6 micrometers.

Another embodied method is a method for producing a particulate composition having enhanced flowability and comprising from about 50 to about 95 weight percent of the embodied particulate compositions of components selected from dithiocarbamates and bisdithiocarbamoyl disulfides, said method comprising (1) producing a first slurry comprising
  (a) particles of said components selected from dithiocarbamates (preferably manganese dithiocarbamate) and bisdithiocarbamoyl disulfides, preferably in a weight percent of at least about ten percent of the weight of the slurry,
  (b) one or more water soluble zinc salt(s), preferably zinc chloride and/or zinc sulphate, and
  (c) water;

(2) wet-milling said first slurry to produce a second slurry having a median particle size of about 2 to about 7 micrometers; and (3) spray-drying said second slurry to produce said particulate composition with a moisture content of about 2 to about 10 weight percent of the embodied particulate composition.

In one preferred method the first slurry comprises
(a) at least ten (10) weight percent of a wet cake of maneb;
(b) manganese ions and zinc ions in a respective mole ratio of about ten to one; and
(c) at least about forty (40) weight percent of water.

Even more preferably, the first slurry has at least about fifty (50) weight percent of a wet cake of maneb and the second slurry has a median particle size of about 5 micrometers.

In further embodiments, the first slurry composition further comprises at least about 2 weight percent of one or more additive(s) selected from stabilizing agents, dispersing agents, anti-foam agents, wetting agents, binding agents, filler agents and extending agents.

The following experiments illustrate embodiments of the present invention but are not intended to limit the scope thereof.

Experiment 1—Production of Dithiocarbamate Slurries

Formulation of nine dithiocarbamate slurries was performed by admixing components to create each slurry with about the following composition:

| Component | Weight percent |
|---|---|
| Wet Cake (about 60% Mn EBDC*) | 72.07 |
| Dispersant** | 2.60 |
| Antifoam agent | 0.02 |
| Hexamethylenetetramine Stabilizer | 1.42 |
| ZnSO4.7H2O | 4.85 |
| Water | 19.04 |

*"Mn EBDC" - manganese ethylenebisdithiocarbamate
**The production for each slurry was the same except that the slurries for samples 1-D, 1-W, 2-W, 3-W and 4-W had Wafex ™ dispersant as the dispersant and the slurries for samples 1-R, 2-R, 3-R and 4-R had Reax 100M ™ dispersant as the dispersant.

After creation, each slurries were then wet-milled to a median particle size of about five (5) micrometers.

Experiment 2—Production of Sample 1-D Composition

The slurry for Sample 1-D from experiment 1 was spray dried with an inlet temperature of about 320°–330° C. and an outlet temperature of about 80° C. to produce an intermediate composition which was subjected to a second drying stage to produce Sample 1-D.

Experiment 3—Production of Sample 1-W, 2-W, 3-W, 4-W, 1-R, 2-R, 3-R and 4-R Compositions The procedure from experiment 1 was used to produce eight (8) slurry samples, e.g., 1-W, 2-W, 3-W, and 4-W for the first set and 1-R, 2-R, 3-R, and 4-R for the second set. The eight slurry samples were then treated to a single spray-drying without a second drying stage. The respective spray drying conditions were an inlet temperature of 320°–330° C. and the following outlet temperatures:

| Samples | Outlet Temperature |
| --- | --- |
| 1-W, 1-R | 115° C. |
| 2-W, 2-R | 100° C. |
| 3-W, 3-R | 90° C. |
| 4-W, 4-R | 70° C. |

TABLE I

| Sample No. | $H_2O$ (%)* | Particle Size** (μm) 50%* | 90%* | ETU*** (%)* |
| --- | --- | --- | --- | --- |
| Initial Properties | | | | |
| 1-D | 0.9 | 6.0 | 12.5 | 0.12 |
| 1-W | 3.3 | 5.9 | 17.8 | 0.13 |
| 1-R | 4.0 | 6.4 | 17.3 | 0.13 |
| 2-R | 6.8 | 6.3 | 17.9 | 0.12 |
| 2-W | 7.0 | 5.6 | 17.2 | 0.097 |
| 3-R | 9.8 | 7.2 | 18.9 | 0.071 |
| 3-W | 10.3 | 6.2 | 18.0 | 0.087 |
| 4-R | 12.0 | 14.9 | 48.6 | 0.057 |
| 4-W | 13.1 | 14.9 | 43.1 | 0.024 |

| Sample No. | $H_2O$ (%) | Particle Size (μm) 50% | 90% | ETU (%) |
| --- | --- | --- | --- | --- |
| After 2 weeks at 54° C. | | | | |
| 1-D | 0.79 | 6.0 | 12.4 | 0.28 |
| 1-W | 2.7 | 7.2 | 22.7 | 0.22 |
| 1-R | 2.7 | 5.5 | 16.2 | 0.24 |
| 2-W | 6.8 | 6.4 | 19.8 | 0.20 |
| 2-R | 6.8 | 7.9 | 23.6 | 0.16 |
| 3-R | 9.1 | 9.7 | 26.9 | 0.15 |
| 3-W | 9.4 | 8.0 | 23.3 | 0.17 |
| 4-R | 10.1 | 41.6 | 77.5 | 0.10 |
| 4-W | 10.3 | 27.1 | 61.9 | 0.11 |
| After 4 weeks at 54° C. | | | | |
| 1-D | 0.80 | 6.5 | 13.3 | 0.20 |
| 1-W | 2.8 | 11.5 | 31.6 | 0.14 |
| 1-R | 3.2 | 8.5 | 27.3 | 0.14 |
| 2-W | 7.3 | 9.1 | 28.6 | 0.12 |
| 2-R | 7.1 | 12.9 | 35.6 | 0.082 |
| 3-R | 10.1 | 13.1 | 37.5 | 0.089 |
| 3-W | 10.2 | 16.1 | 39.1 | 0.068 |
| 4-R | 11.1 | 30.8 | 51.1 | 0.023 |
| 4-W | 10.5 | 40.9 | 73.2 | 0.011 |

*For the entire Table I all $H_2O$ and ETU "%" are by weight and all Particle Size "%" are by volume.
**After redispersion in $H_2O$.
***ETU is ethylenethiourea Experiment 4—Dry Particle Size Analysis Particle size analysis was performed to compare the particle size distribution in a low moisture dithiocarbamate composition (Sample A, same as 1-D hereinabove) and a relatively higher moisture dithiocarbamate composition (Sample B, prepared substantially same but with higher water content). The samples had the following characteristics:

TABLE II

| Sample | A | B |
| --- | --- | --- |
| $H_2O$ | <1% | 3.7% |
| Median Particle Size | 5.9 μm | 29.9 μm |
| Particle Size Distribution | | |
| 10% | ≦0.8 μm | ≦7.1 μm |
| 50% | ≦5.9 μm | ≦29.9 μm |
| 75% | ≦10.4 μm | ≦42.7 μm |
| 90% | ≦14.9 μm | ≦55.0 μm |

The distribution is charted in FIG. 1, which illustrates a significantly different distribution of particle diameters. Dry particle size analysis of other samples were performed with the following results.

TABLE III

| Sample | $H_2O$% | Median Particle (Micrometer) |
| --- | --- | --- |
| 1-D | <1 | 5.9 |
| 2-W | 7 | 56 |
| 3-W | 10 | 62 |
| 2-R | 7 | 57 |
| 3-R | 10 | 63 |

The following comparison of bulk densities were determined:

TABLE IV

| Sample | $H_2O$(%) | Bulk Density (g/cc) |
| --- | --- | --- |
| 1-D | 0.98 | 0.45 |
| 2-W | 7.0 | 0.71 |

What is claimed is:

1. A particulate composition comprising one or more components selected from dithiocarbamates and bisdithiocarbamoyl disulfides and a moisture content of from about 2.5 to about 20% by weight of the particulate composition such that the resulting particulate compound has a bulk density of at least about 0.75 grams per cubic centimeter.

2. The composition of claim 1 wherein said one or more component is selected from ethylenebisdithiocarbamate metal salts, dimethyldithiocarbamate metal salts, propylenedithiocarbamate metal salts, metiram and thiram.

3. The composition of claim 2 wherein said ethylenebisdithiocarbamate metal salts are mancozeb, maneb and zineb.

4. The composition of claim 3 wherein said ethylenebisdithiocarbamate metal salt is mancozeb.

5. The composition of claim 3 wherein said ethylenebisdithiocarbamate metal salt is maneb or zineb.

6. The composition of claim 2 wherein said dithiocarbamate is thiram or metiram.

7. The composition of claim 2 wherein said dimethyldithiocarbamate metal salt is ziram.

8. The composition of claim 2 wherein the total weight of the one or more components selected from dithiocarbamate and bisdithiocarbamoyl disulfide is from about 20 to about 95 weight percent of said particulate composition.

9. The composition of claim 1 wherein the moisture content is from about 2.5 to about 10% by weight of the composition.

10. The composition of claim 1 wherein the moisture content is comprised of one or more component(s) selected from water, alcohol, ammonia, carbon disulfide and glycol.

11. The composition of claim 10 wherein the moisture content is predominantly water.

12. The composition of claim 11 wherein the moisture content is from about 2.5 to about 10% by weight of the composition.

13. The composition of claim 11 wherein the moisture content is predominantly water of hydration.

14. The composition of claim 1 having an initial ethylenethiourea content of less than about 0.1 weight percent of the composition.

15. The composition of claim 14 wherein said dithiocarbamate comprises mancozeb and said initial ethylenethiourea content is from about 0.01 to about 0.05 weight percent of the composition.

16. The composition of claim 1 wherein the ethylenethiourea content of said particulate composition maintained at a temperature of about 54° C. for two weeks after production of said composition is less than about 0.3 weight percent of the composition.

17. The composition of claim 1 wherein the ethylenethiourea content of said particulate composition maintained at a temperature of about 54° C. for two weeks after production of said composition is from about 0.10 to about 0.25 weight percent of the composition.

18. The composition of claim 1 wherein the ethylenethiourea content of said particulate composition maintained at a temperature of about 54° C. for four weeks after production of said composition is less than about 0.3 weight percent of the composition.

19. The composition of claim 18 wherein the ethylenethiourea content of said particulate composition maintained at a temperature of about 54° C. for four weeks after production of said composition is less than about 0.15 weight percent of the composition.

20. The composition of claim 1 wherein the median dry particle size ranges from about 20 to about 400 micrometers.

21. The composition of claim 20 wherein the volume percent amount of dry particles less than about 15 micrometers is at most about 50 percent of the amount of dry particles present when said composition is dried to 1 percent moisture content.

22. The composition of claim 21 wherein the volume percent amount of dry particles less than 15 micrometers is at most about 25 percent of the amount of dry particles present when said composition is dried to 1 percent moisture content based on total weight of the composition.

23. The composition of claim 21 wherein the volume percent amount of dry particles greater than about 20 micrometers is at least about 50 percent of the amount of dry particles present when said composition is dried to 1 percent moisture content based on total weight of the composition.

24. A method for producing a particulate composition comprising a fungicidally effective amount of from about 20 to about 95 weight percent dithiocarbamate, said method comprising
(1) creating a slurry comprising particles of said dithiocarbamate, said particles having a median particle size of from about 2 to about 7 micrometers; and
(2) spray-drying said slurry to produce said particulate composition with a moisture content of from about 2 to about 10 weight percent;
said creating and spray-drying being effective to significantly enhance the flowability of said particulate composition.

25. The method of claim 24 wherein said dithiocarbamate is mancozeb.

26. The method of claim 25 wherein in the slurry said particles have a median particle size of from about 3 to about 6 micrometers.

27. A method for producing a particulate composition having enhanced flowability and comprising a fungicidally effective amount of from about 50 to about 95 weight percent of a dithiocarbamate, said method comprising
(1) producing a first slurry comprising
 (a) particles of manganese dithiocarbamate,
 (b) one or more water soluble zinc salt(s), and
 (c) water;
 wet-milling said first slurry to produce a second slurry having a median particle size of about 2 to about 7 micrometers; and
(3) spray-drying said second slurry at an outlet temperature of less than about 115° C. to produce said particulate composition with a moisture content of about 2 to about 10 weight percent and a bulk density of at least about 0.75 grams/cubic centimeter.

28. The method of claim 27 wherein said first slurry comprises
(a) at least ten (10) weight percent of a wet cake of maneb;
(b) manganese ions and zinc ions in a respective mole ratio of about ten to one; and
(c) at least about forty (40) weight percent of water.

29. The method of claim 28 wherein said first slurry has at least about fifty (50) weight percent of a wet cake of maneb and said second slurry has a median particle size of about 5 micrometer.

30. The method of claim 27 wherein the dithiocarbamate is present in said first slurry in a weight percent of at least about ten percent of the slurry.

31. The method of claim 27 wherein said first slurry composition further comprises at least about 2 weight percent of one or more additive(s) selected from stabilizing agents, dispersing agents, anti-foam agents, wetting agents, binding agents, filler agents and extending agents.

32. The method of claim 27 wherein said one or more water soluble zinc salt(s) comprises zinc chloride and/or zinc sulphate.

33. A composition comprising
(a) particles comprising one or more components selected from ethylenebisdithiocarbamate metal salts, dimethyldithiocarbamate metal salts, propylenedithiocarbamate metal salts, metiram and thiram, and
(b) water from about 2.5 to about 20% by weight of said composition;
wherein the total weight of said components is from about 20 to about 90 weight percent of said composition and
wherein said composition has a bulk density of at least about 0.75 gram per cubic centimeter and the character of an angle of repose of at most about sixty degrees and
wherein at least about fifty percent by volume of said particles as dry particle have a diameter greater than five micrometers.

* * * * *